(12) United States Patent
Calvert

(10) Patent No.: US 8,114,357 B2
(45) Date of Patent: Feb. 14, 2012

(54) APPARATUS FOR SANITIZING WRITING UTENSILS

(76) Inventor: Keith Ray Calvert, Richmond, MO (US)

( * ) Notice: Subject to any disclaimer, the term of this patent is extended or adjusted under 35 U.S.C. 154(b) by 656 days.

(21) Appl. No.: 12/274,289

(22) Filed: Nov. 19, 2008

(65) Prior Publication Data
US 2010/0124520 A1    May 20, 2010

(51) Int. Cl.
*A61L 2/18* (2006.01)
(52) U.S. Cl. ............... 422/292; 422/28; 422/300
(58) Field of Classification Search ......... 422/300, 422/28, 292; 401/130, 208
See application file for complete search history.

(56) References Cited

U.S. PATENT DOCUMENTS

| | | |
|---|---|---|
| 1,653,286 A | 12/1927 | Huggins |
| 1,925,605 A | 9/1933 | Roberts et al. |
| 2,004,805 A | 6/1935 | D'Agostino |
| 2,544,007 A | 3/1951 | Cook |
| 2,578,944 A | 12/1951 | Ramont |
| 3,783,990 A | 1/1974 | Siciliano |
| 4,620,502 A | 11/1986 | Kimble |
| 4,697,390 A | 10/1987 | Ruopsa |
| 5,683,655 A | 11/1997 | Carter |
| 7,811,019 B2 * | 10/2010 | Yoder ................ 401/6 |
| 2007/0131705 A1 | 6/2007 | Behravesh |
| 2009/0148358 A1* | 6/2009 | Wind ............... 422/186.3 |

OTHER PUBLICATIONS

International Search Report dated Jan. 13, 2010 for PCT/US2009/064815, filed Nov. 17, 2009.

* cited by examiner

*Primary Examiner* — Sean E Conley
(74) *Attorney, Agent, or Firm* — Shook, Hardy & Bacon L.L.P.

(57) ABSTRACT

A sanitizing apparatus is provided for automatically sanitizing writing utensils. The sanitizing apparatus transfers disinfectant solution to the writing utensil as the writing utensil is conveyed through a sanitizing chamber on a conveyor belt. The conveyor belt absorbs disinfectant solution when it passes through a basin containing the disinfectant solution and then transfers it to the writing utensil. Once sanitized, the writing utensil is discharged into a retrieval basin where it can be removed by a person wanting to use the writing utensil.

20 Claims, 8 Drawing Sheets

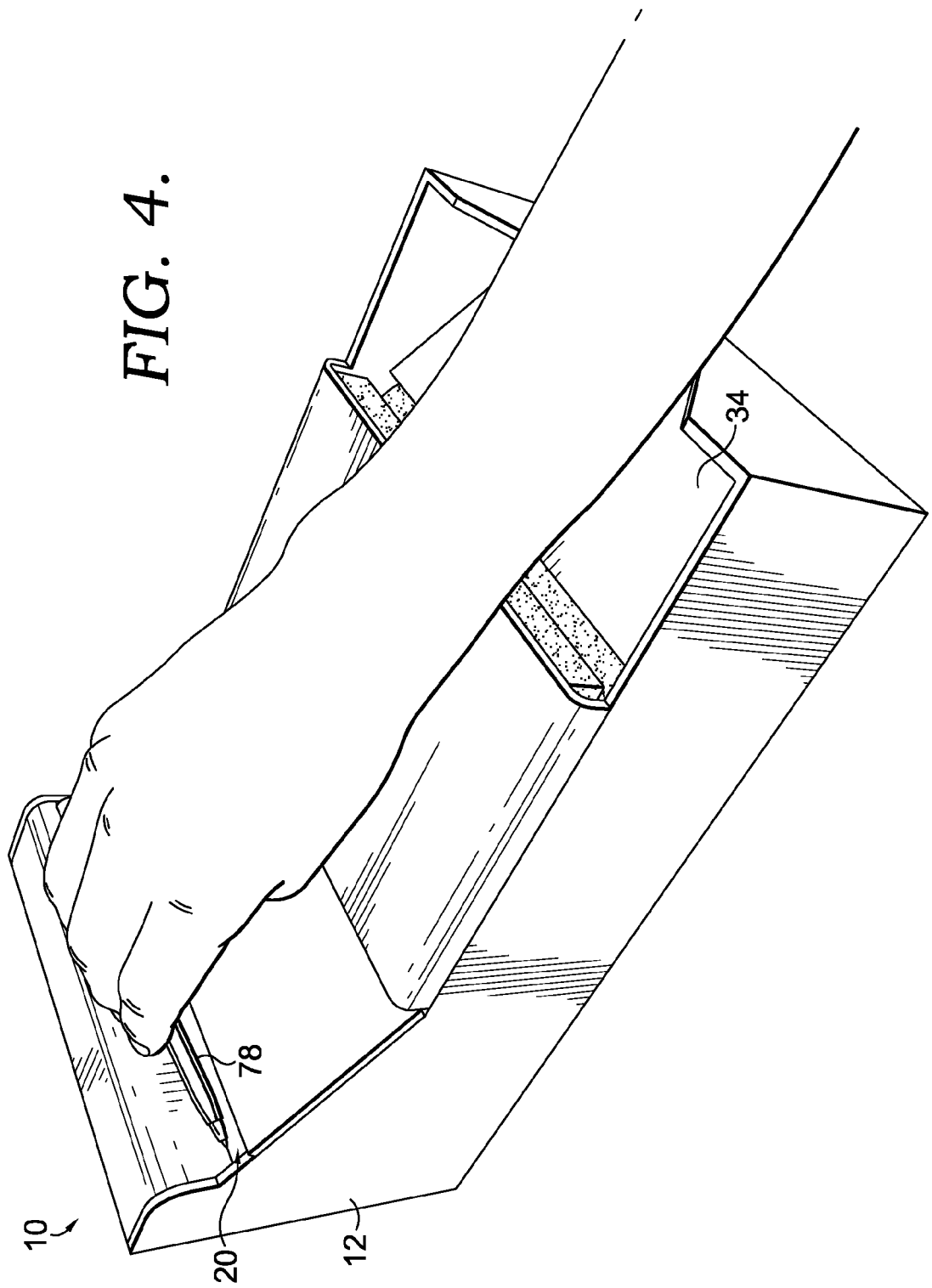

US 8,114,357 B2

APPARATUS FOR SANITIZING WRITING UTENSILS

CROSS-REFERENCE TO RELATED APPLICATIONS

None

STATEMENT REGARDING FEDERALLY SPONSORED RESEARCH OR DEVELOPMENT

Not applicable.

SUMMARY OF THE INVENTION

The present invention relates to a sanitizing apparatus for automatically sanitizing writing utensils. In short, the apparatus receives a writing utensil and conveys the writing utensil through a sanitizing chamber on a conveyor having an absorbent conveyor belt. The absorbent conveyor belt absorbs disinfectant solution as it passes through or by a bath of disinfectant. The writing utensil is sanitized when the disinfectant solution is transferred from the conveyor belt to the writing utensil. The sanitized writing utensil is deposited into a receptacle from which the writing utensil may be retrieved. The sanitizing apparatus may contain a controller that activates the conveyor upon detecting the insertion of a writing utensil into the sanitizing apparatus.

BRIEF DESCRIPTION OF THE SEVERAL VIEWS OF THE DRAWINGS

The present invention is described in detail below with reference to the attached drawing figures, wherein:

FIG. 4 is a perspective view of a user inserting a writing utensil into the sanitizing apparatus of FIG. 1;

DETAILED DESCRIPTION OF THE INVENTION

Figure 1:
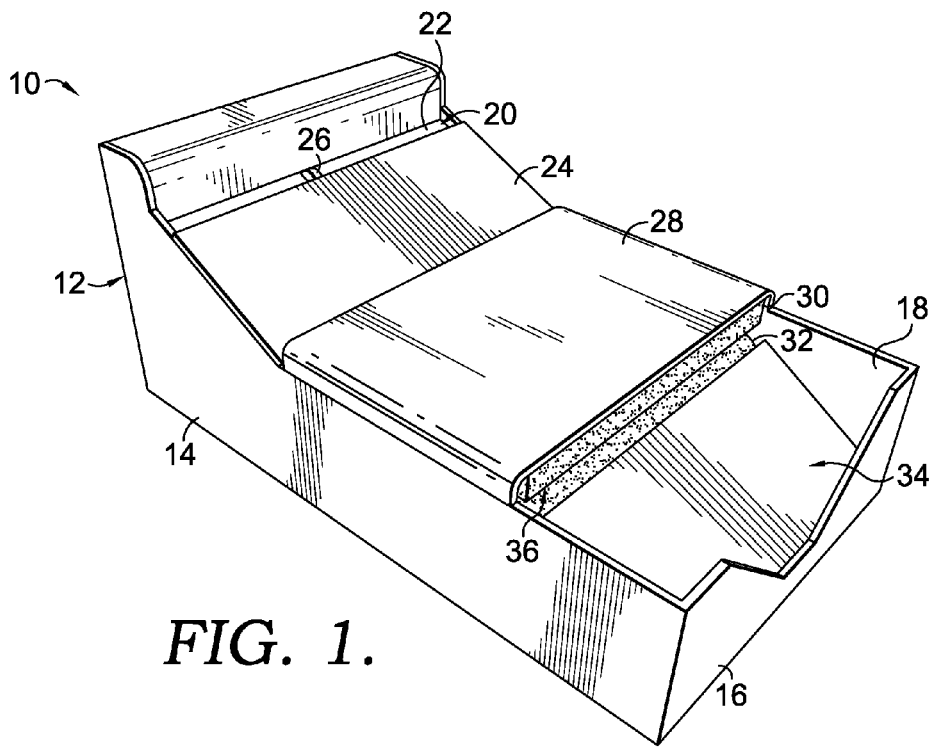
FIG. 1 is a perspective view of a sanitizing apparatus suitable for automatically sanitizing a writing utensil in accordance with an embodiment of the present invention.

Reference will now be made to the accompanying drawings which illustrate an embodiment of a sanitizing apparatus, designated generally by the numeral 10, of the present invention that automatically sanitizes a writing utensil 78. The sanitizing apparatus 10 may be sized to sit on a counter or desk. The sanitizing apparatus 10 includes a receptacle 20 to receive a writing utensil 78. The writing utensil 78 is then conveyed through a sanitizing chamber 90, where disinfectant solution 66 is applied to the writing utensil 78. In one embodiment, the disinfectant solution 66 is transferred to the writing utensil 78 from an absorbent material 33 of the conveyor 32 as the writing utensil 78 is conveyed through the sanitizing chamber 90. The sanitized writing utensil 78 is then discharged into a basin 34 from which it may be retrieved by a person.

Figure 2:
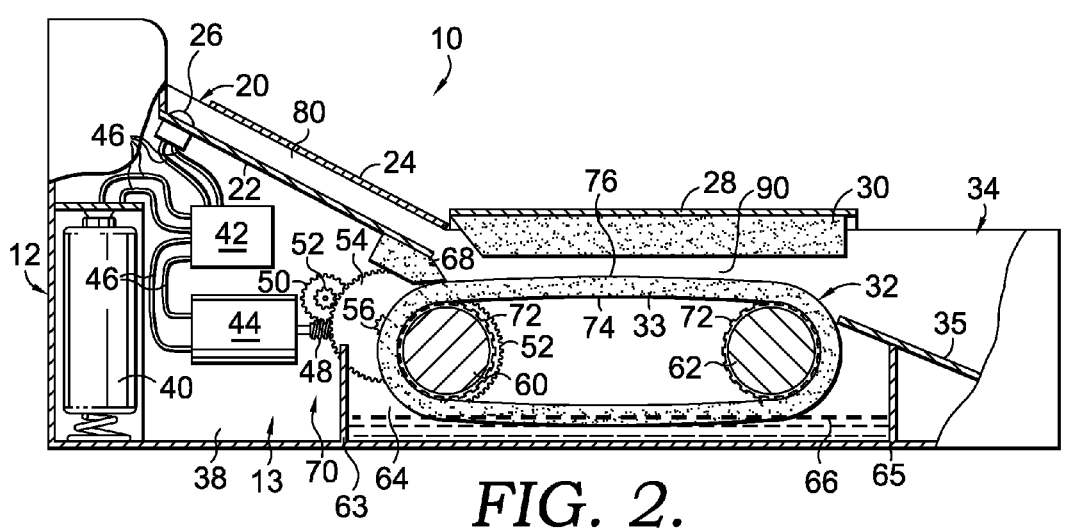
FIG. 2 is a side elevation view in partial cross section illustrating an interior chamber of the sanitizing apparatus of FIG. 1.

Turning now to FIG. 1, a sanitizing apparatus 10 for automatically sanitizing a writing utensil 78 is shown, in accordance with an embodiment of the present invention. FIG. 1 depicts the exterior of sanitizing apparatus 10. The sanitizing apparatus 10 includes a housing 12. The housing 12 may be made of metal, wood, plastic or another suitable material. The housing 12 has a top portion 17, a base portion 11, and a plurality of sidewalls 14, 16, and 18. The top portion 17 includes several different components that may be removable for access to an interior chamber 13 that is described in more detail below. The top portion 17 includes a writing-utensil-conduit top 24, a sanitizing-chamber top 28, and a base portion 35 of the writing utensil retrieval basin 34. The writing-utensil-conduit top 24 may be removed to access a writing utensil conduit 80 (FIG. 2). A user may wish to access the writing utensil conduit 80 for cleaning or maintenance purposes.

The housing 12 includes the writing utensil receptacle 20 which allows a writing utensil to pass from the exterior of the housing 12 into the interior chamber 13 (FIG. 2). The writing utensil receptacle 20 has a length dimension that is longer than a standard sized writing utensil 78 and a width dimension that is wider than a diameter on a standard writing utensil 78. The writing utensil detector 26 detects the insertion of a writing utensil 78 into the writing utensil receptacle 20. The writing utensil detector 26 can be a switch or button, such as the one illustrated in FIG. 5, that can be depressed or it can be a device capable of detecting motion (such as a motion or light detector). The outlet 36 of the sanitizing chamber 90 (FIG. 2) discharges the writing utensil into the writing utensil retrieval basin 34. As explained in more detail below, the writing utensil 78 is sanitized by passing through the sanitizing chamber 90. While in the sanitizing chamber 90 the writing utensil contacts disinfectant solution 66 on the absorbent pad 30, which is attached to the sanitizing-chamber top 28, and conveyor 32, which also includes an absorbent material.

Turning now to FIG. 2, the interior chamber 13 of housing 12 is shown. The interior chamber 13 is defined by the exterior housing 12 walls. The interior chamber 13 is generally segregated into several smaller chambers including the writing utensil conduit 80, the sanitizing chamber 90, the disinfectant basin 64, and the control chamber 38.

The writing utensil conduit 80 receives a writing utensil 78 through the writing utensil receptacle 20 and transfers it via gravity to sanitizing chamber 90. The writing utensil may roll or fall down the writing utensil conduit 80. The writing utensil conduit 80 is defined by the writing-utensil-conduit top 24 and the base portion 22, which is roughly parallel to the writing-utensil-conduit top 24. The writing-utensil-conduit top 24 is spaced greater than a diameter of the writing utensil 78 apart from base portion 22. As described previously, the writing utensil detector 26 is located to detect the insertion of a writing utensil 78 into the writing utensil receptacle 20 and into the writing utensil conduit 80. Though depicted as several inches long in FIG. 2, in other embodiments, the writing utensil conduit 80 may be quite short or absent. In embodiments without a writing utensil conduit 80, the writing utensil receptacle 20 leads directly to the sanitizing chamber 90.

The sanitizing chamber 90 is defined by the sanitizing-chamber top 28 and the conveyor 32. The conveyor 32 includes a conveyor belt 33, a drive pulley 60, and an idle pulley 62. The sanitizing-chamber top 28 is generally parallel to the conveyor 32. The absorbent pad 30 is coupled to an upper surface of the interior of the sanitizing-chamber top 28. The absorbent pad 30 may be formed of any suitable material for absorbing the disinfectant solution 66. For example, the absorbent pad 30 may be a sponge made of rubber, plastic, or cellulose based materials. In an alternative embodiment, a non-absorbent pad 30 is attached to the interior portion of sanitizing-chamber top 28 and used to create the annular space in the sanitizing chamber 90. In one embodiment, the sanitizing-chamber top 28 may be removable from the housing 12. Fasteners such as screws or clips (not shown) may be used to secure the sanitizing-chamber top 28 to the housing 12. The distance between the absorbent pad 30 and conveyor 32 should be slightly less than the diameter of a standard writing utensil 78. This spacing causes the writing utensil 78 to rotate backwards, as indicated by rotational arrow 82 in FIG. 9, as the writing utensil 78 travels through the sanitizing chamber 90.

The disinfectant basin 64 is bounded by the base of the housing 12, a divider wall 63, a divider wall 65, and the bottom of conveyor 32. The divider walls 63, 65 run from side wall 14 to side wall 18 and are generally perpendicular to the side walls 14 and 18. The divider walls 63, 65 and the interior of the disinfectant basin 64 should be constructed of or coated with a material that is compatible with the chosen disinfectant solution 66. The disinfectant basin 64 may have a drain plug (not shown) and a refill port (not shown). In one embodiment, the drain plug is in the base of the sanitizing apparatus 10 and the refill port is in one of the side walls 14 and 18. In one embodiment, the sanitizing solution 66 is an alcohol-based solution that quickly evaporates after being applied to the writing utensil. The level of the sanitizing solution or disinfectant 66 should be high enough such that the bottom of the conveyor belt 33 passes through the disinfectant solution 66 when it is moving. In one embodiment, portions of the side walls are transparent to allow a person to determine the depth of the disinfectant solution 66. In another embodiment, a level gauge (not shown) is attached to the side of the housing 12 to display the disinfectant level. Other mechanisms for showing the disinfectant level are possible.

The conveyor 32 includes the conveyor belt 33, the idle pulley 62, and the drive pulley 60. The drive pulley 60 is rotated by a drive assembly 70. The rotation of the drive pulley 60 causes the conveyor belt 33 to move around the idle pulley 62 and the drive pulley 60. The drive pulley 60 and the idle pulley 62 may be rotate about axles coupled to one or both side walls 14, 18 of housing 12. The conveyor belt 33 includes or is made of an absorbent material that absorbs the disinfectant 66 from the disinfectant basin 64 and transfers it to the writing utensil 78 in the sanitizing chamber 90. In one embodiment, the conveyor belt 33 is constructed of a single absorbent material. In another embodiment, the conveyor belt 33 is constructed from two layers. The first layer is a carcass 74 that provides structural support to interact with the notches 72 on the drive pulley 60 and the idle pulley 62. The second layer may be an absorbent cover 76.

Figure 3:
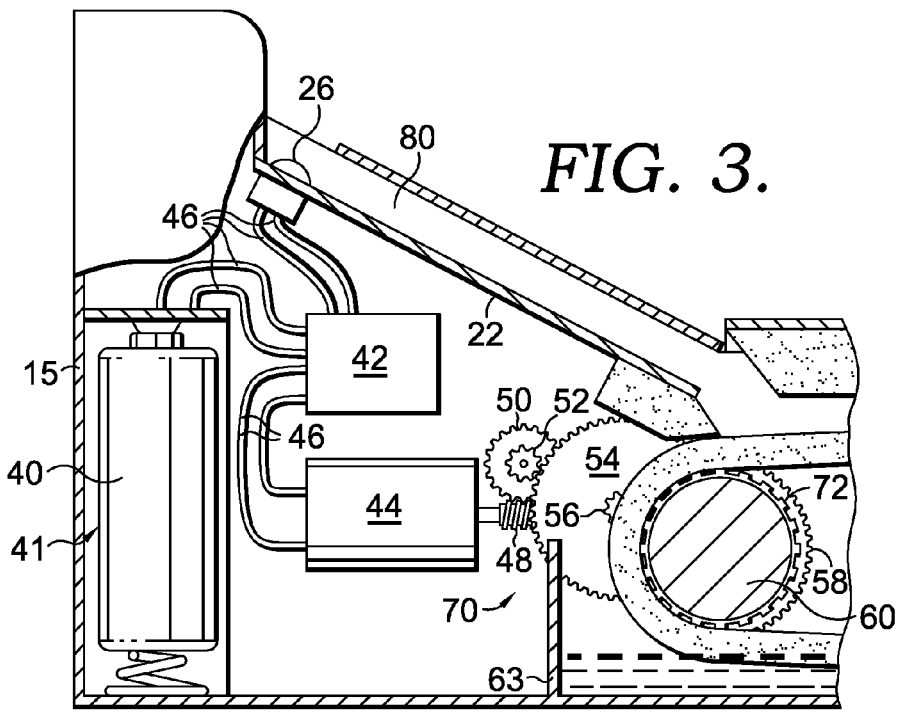
FIG. 3 is a fragmentary side elevation view of a control chamber within the sanitizing apparatus of FIG. 2.

Turing now to FIG. 3, the control chamber 38 within sanitizing apparatus 10 is shown. The control chamber 38 includes a battery chamber 41, a controller 42, a motor 44, and a drive assembly 70. The control chamber 38 is defined by the base portion of housing 12, the divider wall 63, which separates control chamber 38 from disinfectant basin 64, and the base portion 22 of the writing utensil conduit 80. The control chamber 38 may be accessed through a port (not shown) in the base portion of the housing 12 or side walls 14 and 18. In one embodiment, access to the control chamber 38 may be gained through a removable portion of the base portion 22 of the writing utensil conduit 80. The battery chamber 41, the controller 42, the writing utensil detector 26, and the motor 44 are connected by wires 46. The battery chamber 41 includes a battery 40 and may be accessed through the rear side wall 15 of the housing 12. In another embodiment, power may be supplied through connection to an AC circuit using a cord and plug (not shown) that is plugged into an electrical outlet.

The controller 42 activates the motor 44 upon receiving an indication from the writing utensil detector 26 that a writing utensil 78 has been inserted into the writing utensil receptacle 20. As stated, wires 46 connect the controller 42 to the motor 44 and the writing utensil detector 26. The controller 42 may contain a switch that sends power to the motor 44 upon receiving the signal from the writing utensil detector 26. The controller 42 may include a timing mechanism to control the length of time that the power is supplied to the motor 44. After a period of time the controller 42 may stop the conveyor by closing the switch allowing electricity into the motor 44. Alternatively, a detector (not shown) may be provided near the outlet 36 of the sanitizing chamber 90 to detect when the writing utensil 78 leaves the sanitizing chamber 90.

The motor 44 drives the conveyor 32 with the drive assembly 70. The drive assembly 70 includes a worm drive 48 that is coupled to a drive wheel 50. When the worm drive 48 is turned by the motor 44, the grooves in the worm drive 48 move the spokes on drive wheel 50, thereby causing the drive wheel 50 to rotate. The drive wheel 50 is coupled to a drive pinion 52 through a common axle. The spokes in the drive pinion 52 interact with the spokes in the transfer wheel 54, thereby causing the transfer wheel 54 to rotate. The transfer wheel 54 is coupled to the transfer pinion 56 through a common axle. The transfer pinion 56 rotates as transfer wheel 54 rotates. The transfer pinion 56 interacts with the pulley wheel 58, causing the pulley wheel 58 to rotate. The pulley wheel 58 is coupled to the drive pulley 60. The rotation of the drive pulley 60 causes the conveyor belt 33 to move. In the embodiment shown, the idle pulley 62 rotates with the conveyor 32, but is not directly powered.

Figure 5:
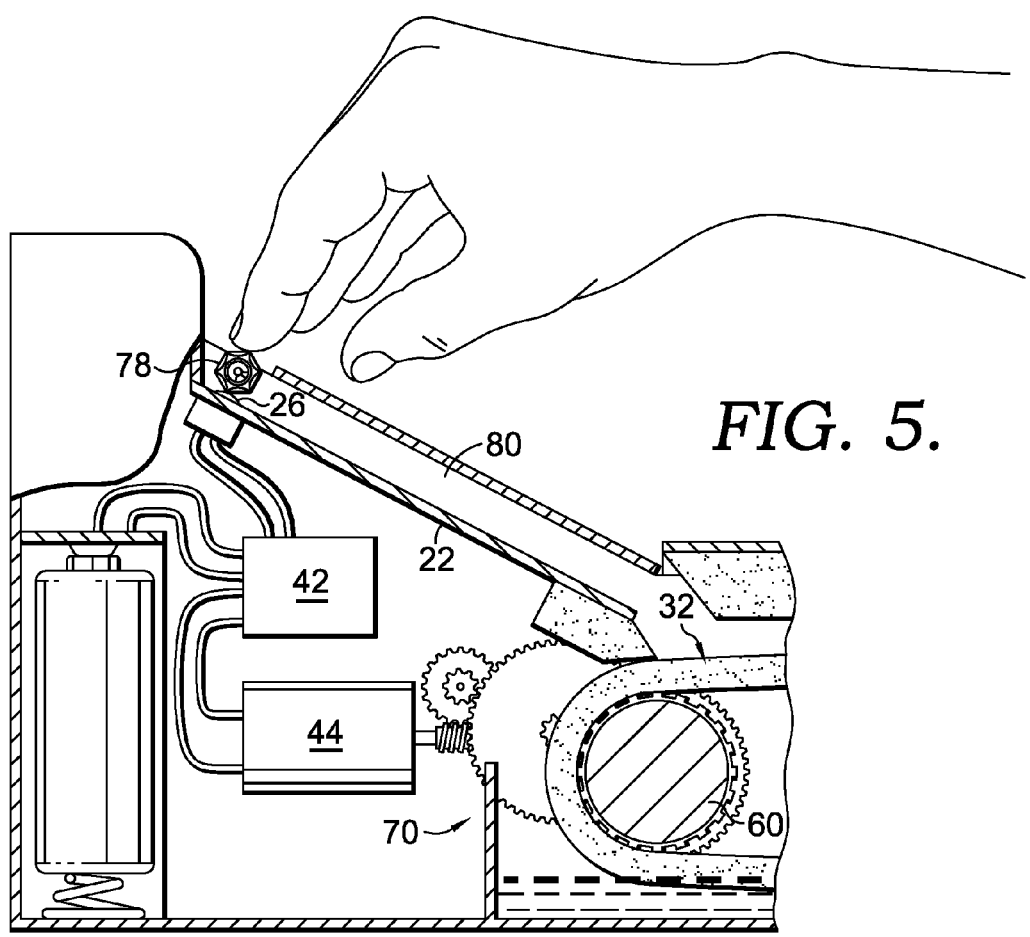
FIG. 5 is a view similar to FIG. 3 illustrating a user inserting a writing utensil into a writing utensil conduit of the sanitizing apparatus.

FIGS. 4-10 illustrate the path a writing utensil 78 takes through the sanitizing apparatus 10. In FIG. 4, a writing utensil 78 is inserted into the apparatus 10 through the writing utensil receptacle 20. Inserting the writing utensil 78 into the writing utensil receptacle 20 activates the writing utensil detector 26. As discussed above, in the illustrated embodiment, the writing utensil detector 26 is a physical switch that is depressed by the insertion of the writing utensil 78. The depression of the writing utensil detector 26 is shown in FIG. 5. FIG. 4 shows the writing utensil detector 26 in its non-compressed state. Embodiments of the present invention are not limited to a writing utensil detector 26 using a switch that must make physical contact with the writing utensil 78. Any device that will detect the insertion of the writing utensil 78 may be used as the writing utensil detector 26. For example, a proximity sensor may be used in embodiments of the present invention as the writing utensil detector 26. As explained previously, the activation of the writing utensil detector 26 causes the controller 42 to activate the motor 44 that starts turning the drive assembly 70, which in turn causes the conveyor 32 to start operating.

Figure 6:
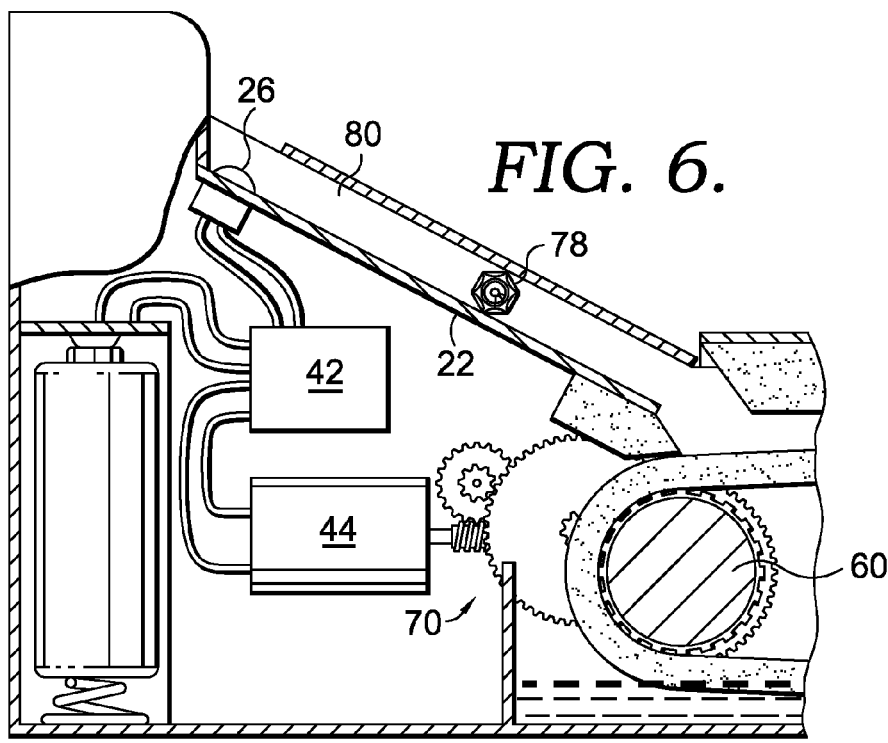
FIG. 6 is a view similar to FIG. 5 illustrating the writing utensil passing through the writing utensil conduit.

Turning now to FIG. 6, the path of the writing utensil 78 through the writing utensil conduit 80 is shown. In the illustrated embodiment, the writing utensil conduit 80 is sloped downward with a sufficient pitch to cause writing utensil 78 to move downward through the writing utensil conduit 80 into sanitizing chamber 90.

Figure 7:
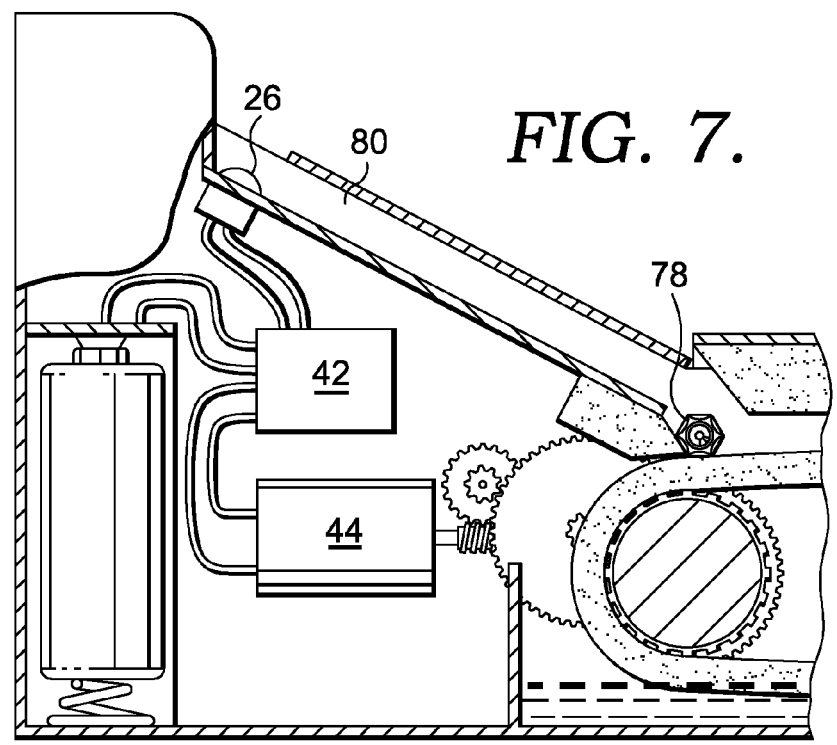
FIG. 7 is a view similar to FIG. 6 illustrating the writing utensil passing from the writing utensil conduit into a sanitizing chamber.

FIG. 7 shows the writing utensil 78 passing through the outlet of the writing utensil conduit 80 and into the inlet of the sanitizing chamber 90. A transition piece 68 separates the control chamber 38 from sanitizing chamber 90 and prevents the writing utensil 78 from falling back into control chamber 38.

Figure 8:
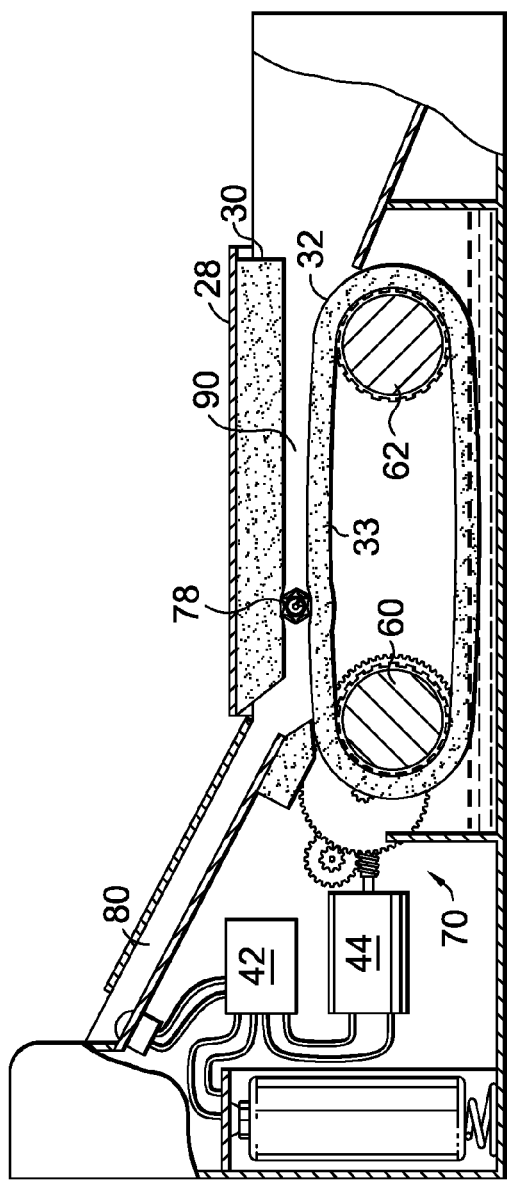
FIG. 8 is a view similar to FIG. 2 illustrating the writing utensil passing through the sanitizing chamber.

Turning now to FIG. 8, the writing utensil 78 passes through the sanitizing chamber 90 where it contacts the disinfectant solution 66 on the conveyor belt 33 and/or the absorbent pad 30. As explained previously, the disinfectant solution 66 may be in both the conveyor belt 33 and absorbent pad 30. The disinfectant 66 may get into the absorbent pad 30 as excess solution is transferred from the writing utensil 78. Also as explained previously, the space between the absorbent pad 30 and the conveyor 32 may be slightly less than the diameter of the writing utensil 78.

Figure 9:
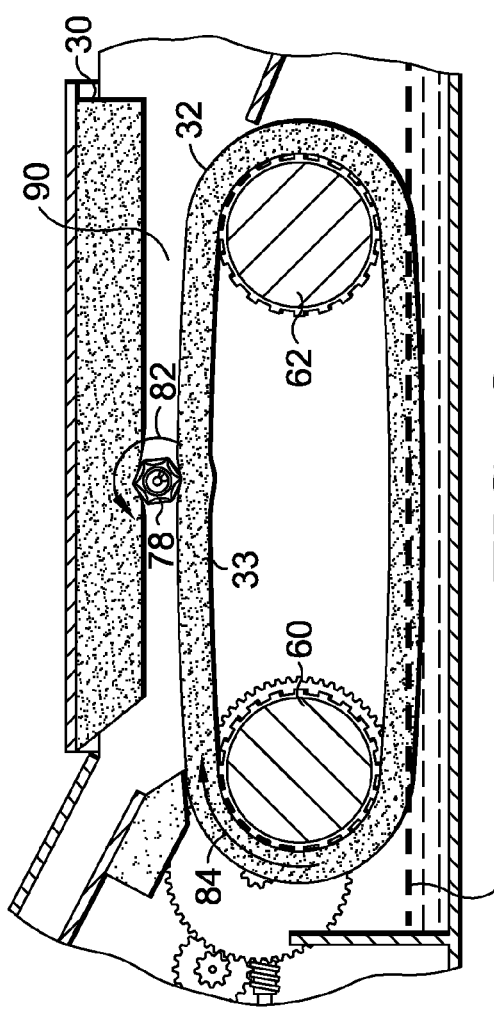
FIG. 9 is an enlarged fragmentary side elevation view of a portion of FIG. 8 illustrating rotation of the writing utensil while it passes through the sanitizing chamber.

As shown in FIG. 9, contact with both the conveyor belt 33 and the absorbent pad 30 causes the writing utensil 78 to rotate, as indicated by rotation arrow 82, while passing through the sanitizing chamber 90. The rotation of writing utensil 78 causes all surfaces on the writing utensil 78 to contact disinfectant solution 66 absorbed into conveyor 32. The space between the absorbent pad 30 and the conveyor 32 may be adjusted in a number of ways to accommodate different diameter writing utensils. For example, the absorbent pad 30 attached to sanitizing-chamber top 28 may be changed to a different thickness pad, to increase or decrease the space between the absorbent pad 30 and the conveyor belt 33. Different absorbent pads may be provided to work with writing utensils having different diameters. In one embodiment, a mechanism to raise and lower the sanitizing-chamber top 28 is included in the housing 12. An adjustable sanitizing-chamber top 28 allows a single absorbent pad 30 to work on different diameter writing utensils.

Figure 10:
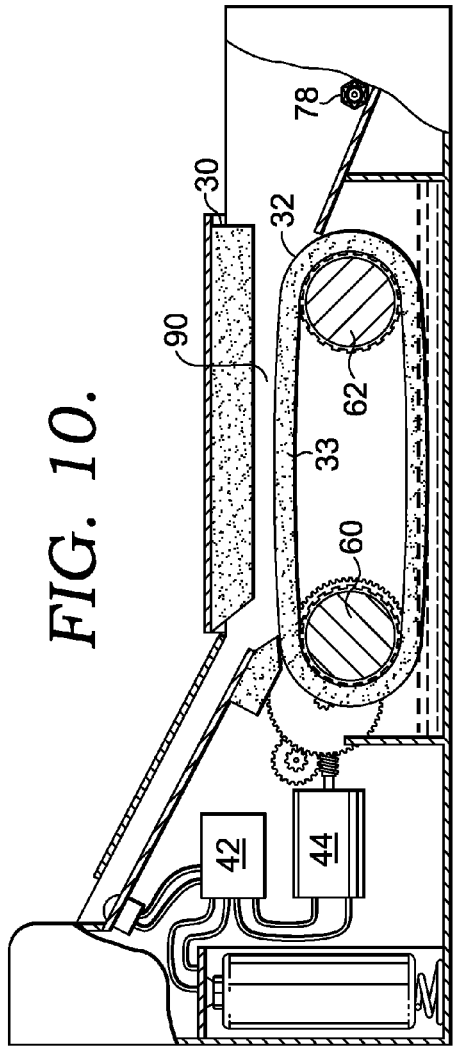
FIG. 10 is a view similar to FIG. 8 illustrating the sanitized writing utensil resting in a writing utensil retrieval basin.

Turning now to FIG. 10, the sanitized writing utensil 78 is shown resting in the writing utensil retrieval basin 34. As explained previously, the writing utensil retrieval basin 34 may be sized to hold multiple writing utensils. A user may access the writing utensil retrieval basin 34 and withdraw a writing utensil 78 with their hand. The writing utensil 78 may then be used. After use, the sanitizing process may be repeated by placing the writing utensil 78 into the writing utensil receptacle 20.

Figure 11:
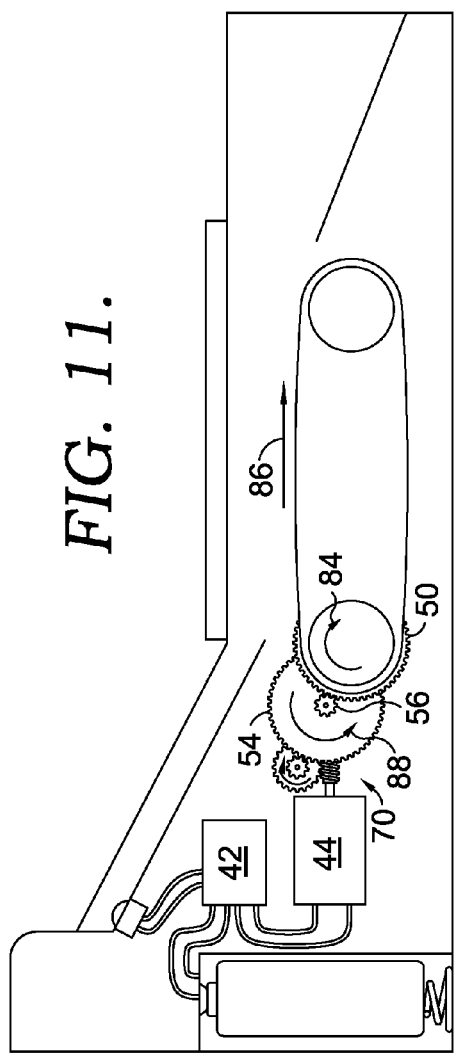
FIG. 11 is a schematic side elevation view illustrating the rotation and movement of selected moving components during operation of the sanitizing apparatus
Figure 12:
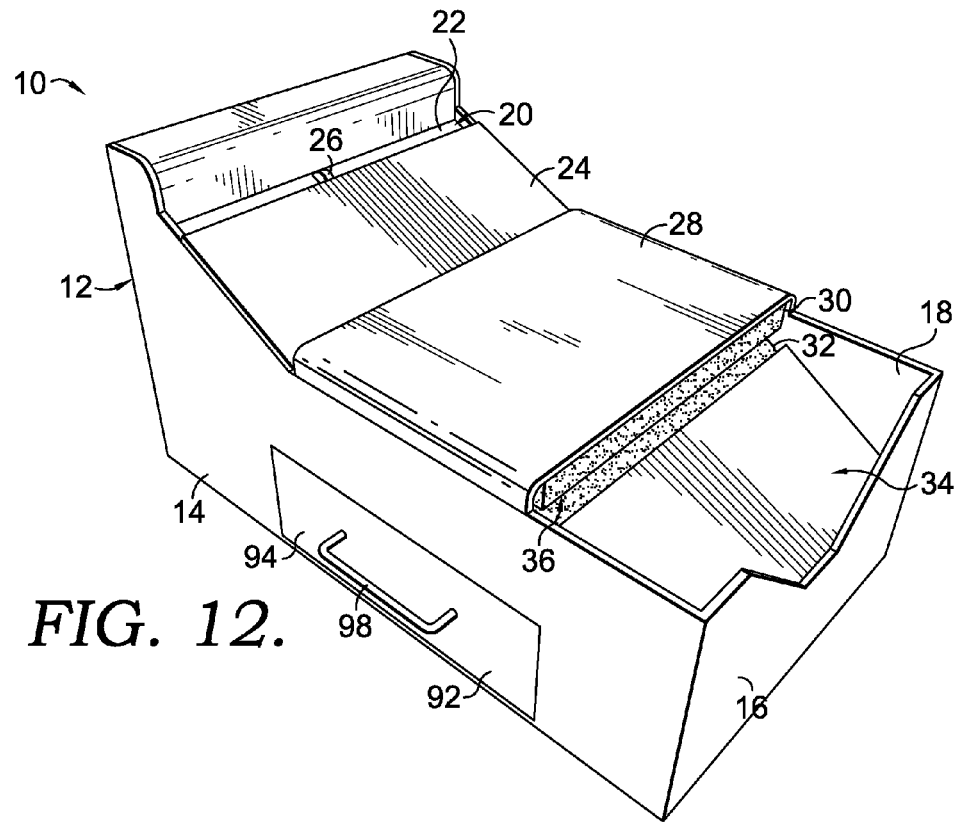
FIG. 12 is a perspective view of second embodiment of a sanitizing apparatus of the present invention.

Turning now to FIG. 11, the rotation of certain moving components within the sanitizing apparatus 10 are shown according to an embodiment of the present invention. Movement arrow 86 indicates the conveyor belt 33 should move in a direction that carries the writing utensil 78 through the sanitizing chamber 90. Rotational arrows 84, 85 and 88 indicate a direction that various components of the drive assembly 70 rotate during an operation of the motor 44.

FIGS. 12-15 illustrate a second embodiment of the sanitizing apparatus of the present invention. In the first embodiment, illustrated in FIGS. 1-11, the disinfectant basin 64 is filled with liquid sanitizing solution 66 via a refill port (not shown) in one of the side walls 14, 18. While this method is effective, pouring liquid sanitizing solution 66 into a refill port can be messy and time consuming.

To make the maintaining of the level of sanitizing solution 66 easier, the second embodiment of the sanitizing apparatus 10' is provided with a pull-out drawer 92 in one of the side walls 14, 18. The drawer 92 has a drawer front 94 and a tray 96. A handle 98 connected to the drawer front 94 allows a user to easily pull the drawer 92 out of the housing 12 to have ready access to the sanitizing solution 66.

While the user may simply use the drawer 92 to provide easier access to the sanitizing solution 66, the second embodiment preferably also includes a replaceable and/or refillable sanitizing solution cartridge 100. The cartridge 100 is sized for receipt in the tray 96 and includes a trough 102 and at least one roller 104.

The trough 102 has a plurality of side walls 106 and a bottom 108 that cooperate to hold the sanitizing solution 66 therein. In the illustrated embodiment, and as best viewed in FIG. 15, mounting flanges 110 are provided on two opposing side walls 106 at an upper periphery 112 thereof. The mounting flanges 110 have a C-shaped opening 114 for receiving an axle 116 of the roller 104. In this manner, the rollers 104 are rotationally supported by the side walls 106 of the trough 102. The C-shaped openings 114 may be of the type where the axle 116 may be "snapped" therein, especially if the trough is made of a plastic material. The trough 102 is preferably sized or constructed to fit snuggly in the tray 96 so as to prevent movement of the cartridge 100 during its insertion into and use of the sanitizing apparatus 10.

Figure 14:
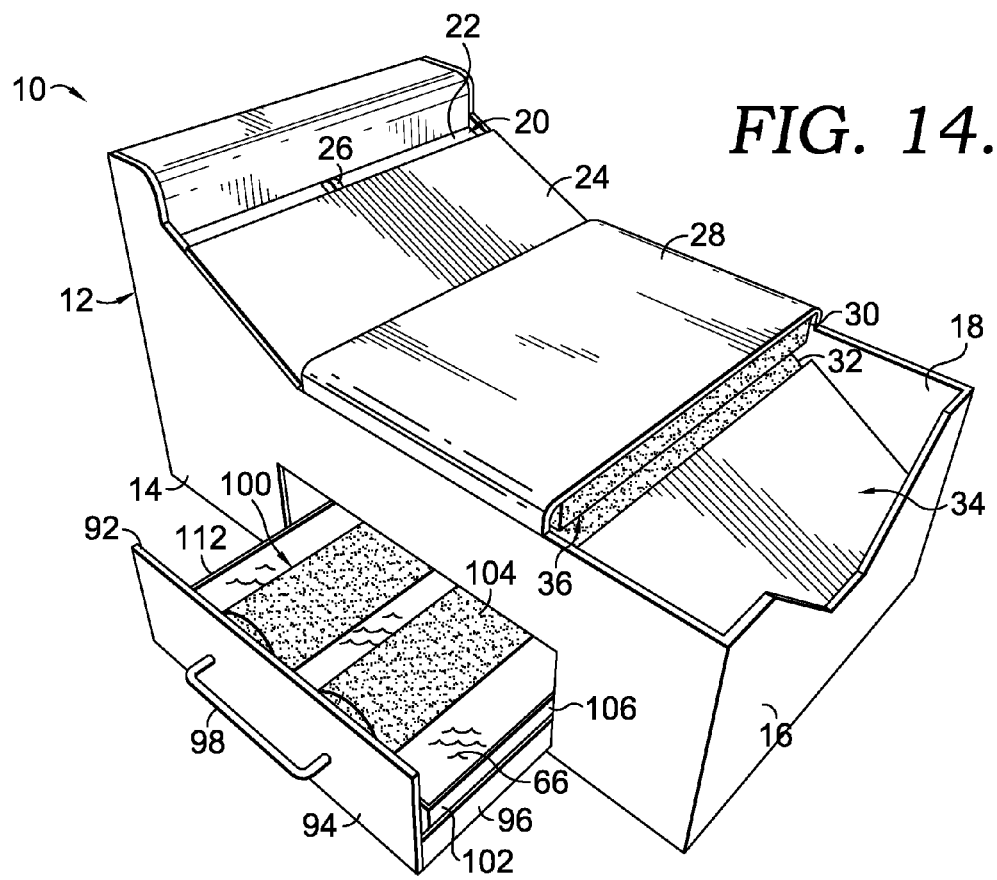
FIG. 14 is a perspective view of the sanitizing apparatus of FIG. 12 with a drawer partially extended and having a sanitizing solution cartridge therein.
Figure 15:
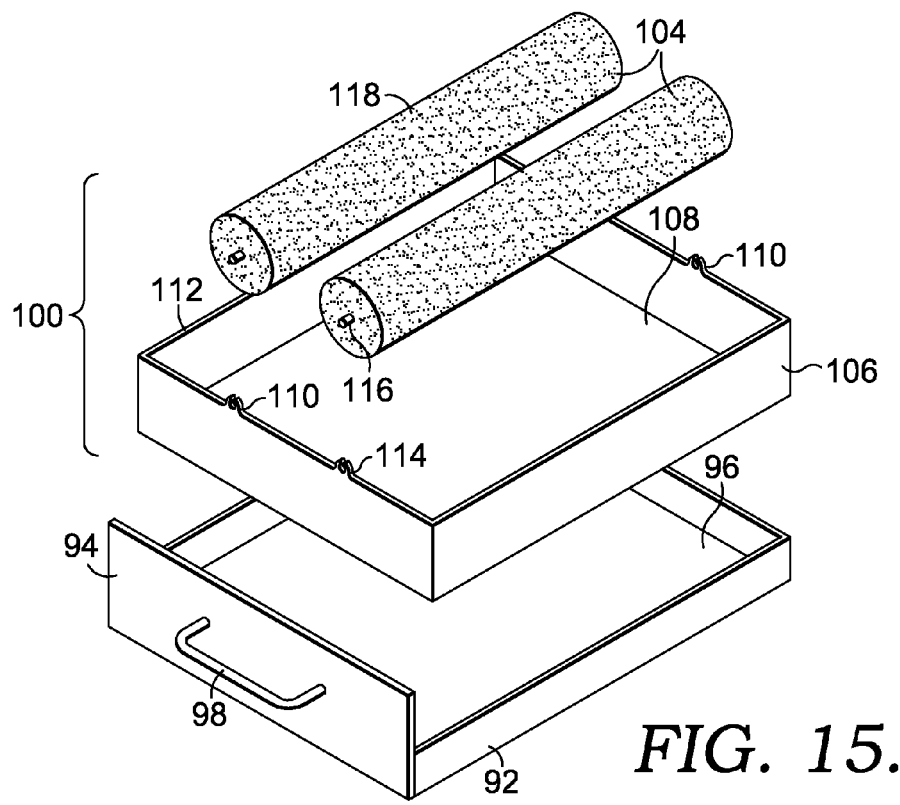
FIG. 15 is an exploded perspective view of the drawer and cartridge of FIG. 14.

To install the cartridge 100, the user simply pulls the drawer 92 out of the housing 12 by the handle 98. The cartridge 100 is then placed in the tray 96 of the drawer 92. The cartridge 100 should be oriented in the tray 96 such that the rollers 106 are transverse to the housing 12 and the direction of travel of the belt 33 and parallel to the pulleys 60, 62, as illustrated in FIG. 14. The trough 102 may then be filled with sanitizing solution 66 or, alternatively, the cartridge may come pre-filled with sanitizing solution 66. If pre-filled, a removable wrap (not shown) may be secured to the upper periphery 112 of the trough 102 to prevent spilling of sanitizing solution 66 during handling.

Figure 13:
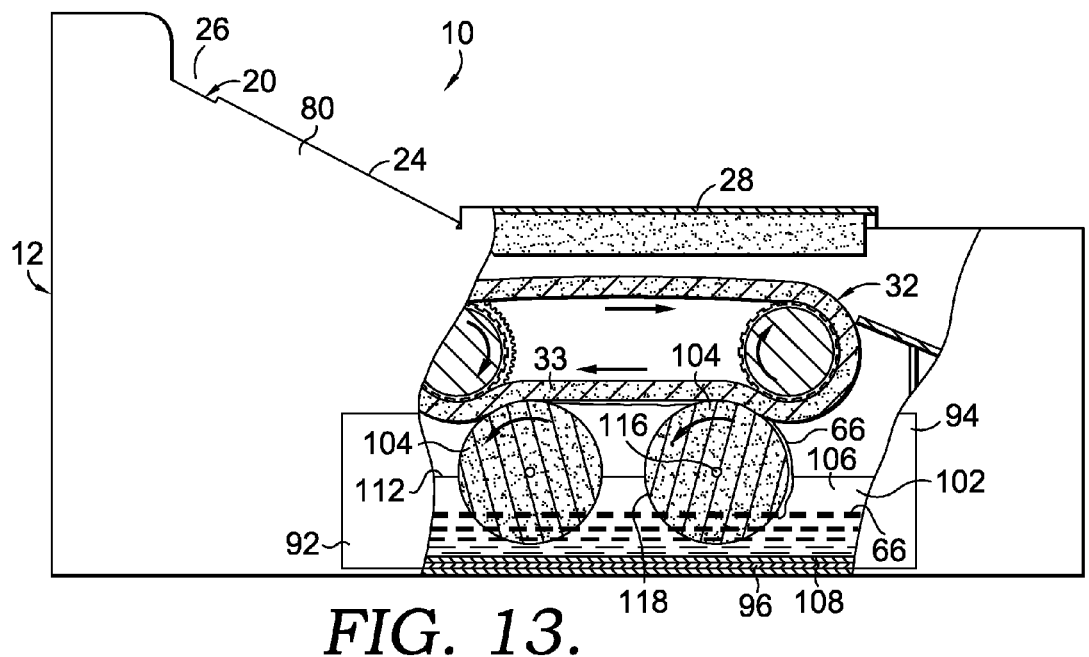
FIG. 13 is a side elevation view in partial cross section illustrating an interior of the sanitizing apparatus of FIG. 12.

With a filled cartridge 100 in the tray 94, the user slides the drawer 92 back into the housing 12. The rollers 104 are sized to extend downwardly into the sanitizing solution 66 contained in the trough 102 and upwardly beyond the upper periphery 112 of the trough 102. When the drawer 92 is fully closed, the cartridge 100 is preferably positioned directly under the belt 33. Further, the rollers 104 extend upwardly an amount such that they come in contact with the belt 33. Preferably, the apex of the rollers 104 is above a normal low point for the belt 33 such that the rollers 104 actually cause the belt 33 to deflect upwardly, as illustrated in FIG. 13.

In this arrangement, when the sanitizing apparatus 10 is activated and the belt 33 begins to move, the frictional relationship between the belt 33 and the rollers 104 causes the rollers 104 to rotate. The lower portions of the rollers 104 travel down into the sanitizing solution 66, where they pick up the sanitizing solution 66 on an outer surface 118 of the rollers 104. The sanitizing solution 66 is then carried upwardly and transferred to the bottom of the belt 33, just as if the belt 33 was passing directly through the sanitizing solution 33 as in the first embodiment discussed above.

Many variations can be made to the illustrated embodiment of the present invention without departing from the scope of the present invention. Such modifications are within the scope of the present invention. For example, while the axles 116 of the rollers 104 are shown in the illustrated embodiment as being supported on top of the side walls 106, it will be readily understood that any other known manner of supporting the rollers 104 such that they may roll would be acceptable. Other modifications would be within the scope of the present invention.

From the foregoing it will be seen that this invention is one well adapted to attain all ends and objects hereinabove set forth together with the other advantages which are obvious and which are inherent to the method and apparatus. It will be understood that certain features and subcombinations are of utility and may be employed without reference to other features and subcombinations. This is contemplated by and is within the scope of the invention.

Since many possible embodiments may be made of the invention without departing from the scope thereof, it is to be understood that all matter herein set forth or shown in the accompanying drawings is to be interpreted as illustrative of applications of the principles of this invention, and not in a limiting sense.

Although the invention has been described with reference to the preferred features of various embodiments illustrated in the attached, and described in the above description, one skilled in the art will recognize that numerous substitutions could be made and the equivalents employed herein without departing from the scope of the invention, which is more properly defined as it is recited in the claims which, of course, are subject to amendment.

The invention claimed is:

1. A sanitizing apparatus for use in automatically sanitizing a writing utensil comprising:
   a housing having an interior chamber defined by a top and a base that are connected together by at least one side wall;
   a writing utensil receptacle positioned in the top of the housing that allows a writing utensil to pass through the top and into the interior chamber;
   a writing utensil conduit within the interior chamber and coupled to the writing utensil receptacle, wherein the writing utensil conduit is a passageway bounded by the top and a base portion having a downward slope sufficient to allow a writing utensil to be carried by gravity through the writing utensil conduit;
   a sanitizing chamber within the interior chamber, wherein a lower portion of the sanitizing chamber is defined by a movable, absorbent conveyor belt and an upper portion of the sanitizing chamber is defined by an absorbent pad located above and generally parallel to the conveyor belt, wherein the sanitizing chamber receives a writing utensil from an outlet in the writing utensil conduit and carries the writing utensil through the sanitizing chamber on the conveyor belt to an outlet in the sanitizing chamber;
   a basin suitable for holding a disinfectant within the interior chamber and underneath the conveyor belt, wherein the conveyor belt passes through the basin; and
   a writing utensil retrieval basin located in a exterior portion of the housing for receiving a sanitized writing utensil from the outlet in the sanitizing chamber and storing the sanitized writing utensil, wherein the writing utensil is accessible to a human hand while in the writing utensil retrieval basin,
   wherein the belt is positioned in the basin to transfer disinfectant from the basin to the writing utensil as the writing utensil passes through the sanitizing chamber during use.

2. The sanitizing apparatus of claim 1, further comprising a writing utensil detector for detecting insertion of a writing utensil into the writing utensil receptacle.

3. The sanitizing apparatus of claim 2, further comprising a controller for activating a motor coupled with a drive mechanism which activates the conveyor belt upon receiving an indication from the writing utensil detector that a writing utensil has been inserted into the writing utensil receptacle.

4. The sanitizing apparatus of claim 3, wherein the controller contains a timer that deactivates the motor after a period of time, wherein the period of time is set to allow the writing utensil to pass through the sanitizing chamber and into the writing utensil retrieval basin before the motor is deactivated.

5. The sanitizing apparatus of claim 2, wherein the writing utensil detector utilizes a proximity sensor to detect insertion of a writing utensil into the writing utensil receptacle, wherein the proximity sensor detects insertion of the writing utensil without requiring physical contact with the proximity sensor.

6. The sanitizing apparatus of claim 1, wherein a distance between the lower portion and the upper portion of the sanitizing chamber is less than a diameter of a writing utensil, whereby the writing utensil compresses the conveyor belt and the absorbent pad as it passes there between and whereby the absorbent pad and the conveyor belt cooperate to cause the writing utensil to rotate as it passes through the sanitizing chamber.

7. The sanitizing apparatus of claim 1, wherein the writing utensil receptacle has a length dimension that is longer than the length dimension of a writing utensil, and wherein the writing utensil receptacle has a width dimension that is wider than a diameter of the writing utensil.

8. The sanitizing apparatus of claim 1, wherein a depth of the disinfectant in the basin causes the conveyor belt to be in contact with the disinfectant.

9. The sanitizing apparatus of claim 1, further comprising a power supply coupled to a motor that drives the conveyor belt.

10. The sanitizing apparatus of claim 9, wherein the power supply is coupled to a conduit for receiving AC power from an electrical outlet.

11. A sanitizing apparatus for automatically sanitizing a writing utensil with a disinfectant solution comprising:
    a housing having an interior chamber formed by a base, one or more top portions, and one or more side walls, the interior chamber partitioned into a control chamber, a sanitizing chamber, and a disinfectant basin, the exterior of the housing having a writing utensil receptacle that allows a writing utensil to pass into the interior chamber and a writing utensil retrieval basin for receiving the writing utensil from the sanitizing chamber, wherein the disinfectant basin is suitable for holding the disinfectant solution and is located underneath the sanitizing chamber;
    a conveyor, within the interior chamber, including an absorbent belt for conveying the writing utensil through the sanitizing chamber, and wherein the conveyor passes through the disinfectant basin, thereby allowing disinfectant to be absorbed onto the absorbent belt and transferred from the belt onto the writing utensil in the sanitizing chamber, wherein the sanitizing chamber is defined by the conveyor and an absorbent pad that is above and generally parallel to the conveyor; and a controller positioned within the control chamber and suitable for activating a drive mechanism coupled with the conveyor upon receiving an indication that a writing utensil has been received in the writing utensil receptacle.

12. The sanitizing apparatus of claim 11, wherein an absorbent pad is attached to a top portion of the housing, thereby forming an annular space in the sanitizing chamber through which a writing utensil passes.

13. The sanitizing apparatus of claim 12, wherein a portion of the conveyor defines a lower boundary of the sanitizing chamber and a top boundary of the disinfectant basin, and wherein a top portion of the sanitizing chamber is formed by the absorbent pad attached to the top portion of the housing, whereby the writing utensil compresses the absorbent belt and the absorbent pad as it passes there between and whereby the absorbent pad and the absorbent belt cooperate to cause the writing utensil to rotate as it passes through the annular space of the sanitizing chamber.

14. The sanitizing apparatus of claim 11, further comprising a writing utensil detector for detecting insertion of a writing utensil into the writing utensil receptacle, wherein the writing utensil detector is located adjacent to the writing utensil receptacle.

15. The sanitizing apparatus of claim 14, wherein the writing utensil detector is a proximity sensor.

16. The sanitizing apparatus of claim 14, wherein the controller causes the conveyor to run for a fixed period of time upon receiving a signal from the writing utensil detector indicating that a writing utensil has been inserted into the writing utensil receptacle.

17. A sanitizing apparatus having a housing that defines an interior chamber containing components for automatically sanitizing a writing utensil comprising:

a basin for holding a disinfectant;

a conveyor for conveying the writing utensil to be sanitized, wherein the conveyor includes an absorbent belt that is suitable for absorbing the disinfectant from the basin and transferring it from the belt to the writing utensil; and a sanitizing chamber having a lower portion defined by the conveyor and a top portion defined by a cover including an absorbent material, wherein the top portion is positioned above and generally parallel to the conveyor, wherein the top portion is spaced a distance less than the diameter of the writing utensil above the conveyor, thereby causing the writing utensil to rotate as the writing utensil is conveyed through the sanitizing chamber by the conveyor to distribute the coating of the writing utensil with the disinfectant along an outer surface of the writing utensil as it rolls along the conveyor.

18. The sanitizing apparatus of claim 17, further comprising a controller that causes the conveyor to move upon receiving a signal indicating a writing utensil has been inserted into the sanitizing apparatus.

19. The sanitizing apparatus of claim 18, further comprising a drawer, wherein the basin for holding the disinfectant is positioned in the drawer, and wherein the drawer may be pulled out of the housing to provide access to the basin.

20. The sanitizing apparatus of claim 19, wherein the basin is a trough, wherein the trough is part of a cartridge further including at least one roller, wherein the roller is supported by the trough, wherein the roller selectively interacts with the belt, and wherein the roller transfers the disinfectant from the trough to the belt.

* * * * *